United States Patent [19]

Miller

[11] Patent Number: 5,728,719

[45] Date of Patent: Mar. 17, 1998

[54] SYSTEMIC CONTROL OF PARASITES

[75] Inventor: Thomas A. Miller, Carrollton, Tex.

[73] Assignee: Virbac, Inc., Ft. Worth, Tex.

[21] Appl. No.: 403,414

[22] Filed: Mar. 14, 1995

Related U.S. Application Data

[62] Division of Ser. No. 210,135, Mar. 17, 1994, Pat. No. 5,439,924, which is a continuation of Ser. No. 980,591, Nov. 23, 1992, abandoned, which is a continuation-in-part of Ser. No. 812,430, Dec. 23, 1991, abandoned.

[51] Int. Cl.$^6$ .................................................. A01N 43/82
[52] U.S. Cl. .................. 514/360; 514/521; 514/298; 514/667; 514/594; 514/354; 514/245; 514/369; 514/241; 514/219; 514/450; 514/712; 514/452; 501/123; 549/264; 424/405; 568/363; 568/592
[58] Field of Search .................... 514/360, 521, 514/298, 667, 594, 354, 245, 369, 241, 219, 450, 712, 452; 501/123; 549/264; 424/405; 568/636, 592

[56] References Cited

U.S. PATENT DOCUMENTS

| | | | |
|---|---|---|---|
| 3,748,356 | 7/1973 | Wellinga et al. | 564/44 |
| 3,950,360 | 4/1976 | Aoki et al. | 549/264 |
| 3,962,458 | 6/1976 | Schrider | 514/54 |
| 3,987,102 | 10/1976 | Karrer | 568/331 |
| 3,987,108 | 10/1976 | Karrer | 568/631 |
| 3,988,477 | 10/1976 | Karrer | 514/712 |
| 4,006,236 | 2/1977 | Schrider | 514/298 |
| 4,007,280 | 2/1977 | Karrer | 514/452 |
| 4,017,549 | 4/1977 | Karrer et al. | 568/640 |
| 4,031,239 | 6/1977 | Schrider | 514/521 |
| 4,053,631 | 10/1977 | Schrider | 514/521 |
| 4,057,587 | 11/1977 | Karrer et al. | 568/636 |
| 4,060,629 | 11/1977 | Karrer | 514/489 |
| 4,061,683 | 12/1977 | Karrer et al. | 514/489 |
| 4,080,470 | 3/1978 | Karrer | 514/489 |
| 4,089,975 | 5/1978 | Wade et al. | 514/594 |
| 4,092,365 | 5/1978 | Farooq et al. | 568/592 |
| 4,092,421 | 5/1978 | Wade et al. | 514/354 |
| 4,097,581 | 6/1978 | Farooq et al. | 514/467 |
| 4,100,296 | 7/1978 | Farooq et al. | 514/467 |
| 4,160,831 | 7/1979 | Laanio et al. | 514/236.2 |
| 4,160,832 | 7/1979 | Laanio et al. | 514/236.2 |
| 4,166,107 | 8/1979 | Miller et al. | 424/405 |
| 4,172,146 | 10/1979 | Karrer | 514/543 |
| 4,173,638 | 11/1979 | Nishiyama et al. | 514/351 |
| 4,187,304 | 2/1980 | Immler et al. | 514/245 |
| 4,187,305 | 2/1980 | Immler et al. | 514/245 |
| 4,199,569 | 4/1980 | Chabala et al. | 514/30 |

(List continued on next page.)

FOREIGN PATENT DOCUMENTS

| | | |
|---|---|---|
| 0008540 | 3/1980 | European Pat. Off. |
| 0037092 | 10/1981 | European Pat. Off. |
| 0169169 | 5/1985 | European Pat. Off. |
| 3825172 | 7/1988 | France . |
| 2084574 | 9/1981 | United Kingdom . |
| 2102425 | 7/1982 | United Kingdom . |
| 8603941 | 7/1986 | WIPO . |

OTHER PUBLICATIONS

Chemical Abstracts 102:57842e (1985).
Chemical Abstracts 102:61919c (1985).

*Primary Examiner*—Karen A. Dean
*Attorney, Agent, or Firm*—Martin L. McGregor

[57] ABSTRACT

The present invention is a method for controlling ectoparasites. More particularly, the invention relates to a method of treatment in which the warm blooded animal is dosed with an ovicidally effective amount of a heterocyclic nitrogen compound selected from the group represented by the formula:

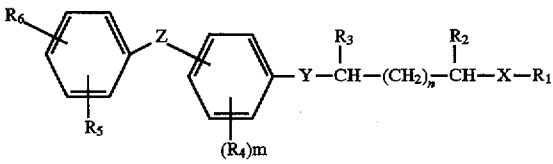

wherein $R_1$, is either one of the following groups:

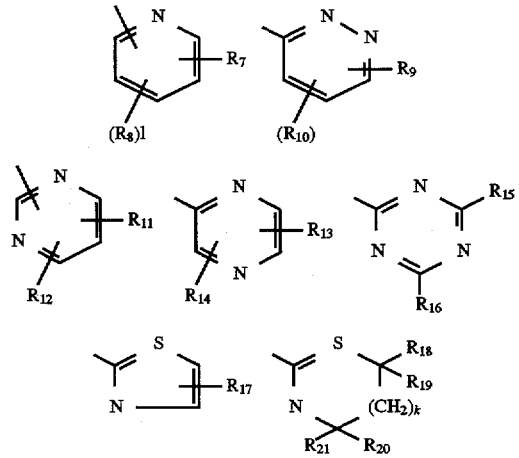

in which $R_7$, $R_8$, $R_9$, $R_{10}$, $R_{11}$, $R_{12}$, $R_{13}$, $R_{14}$, $R_{15}$, $R_{16}$, and $R_{17}$ are, the same or different, each a hydrogen atom, a halogen atom, a $C_1$–$C_4$ alkoxy group, a $C_1$–$C_4$ alkylthio group, a trifluoro methyl group or a vitro group, $R_{18}$, $R_{19}$, $R_{20}$ and $R_{21}$ are, the same or different, each a hydrogen atom or a methyl group, k is an integer of 0 to 1 and l is an integer of 0 to 3; $R_2$ and $R_3$ are, the same or different, each a hydrogen atom, a halogen atom or a methyl group; $R_4$ is a halogen atom or a methyl group; $R_5$ and $R_6$ are, the same or different, each a hydrogen atom, a halogen atom, a $C_1$–$C_4$ haloalkyl group or a $C_1$–$C_4$ haloalkoxy group; X, Y and Z are, the same or different, each an oxygen atom, a sulfur atom or a methylene group, m is an integer of 0 to 4, and n is an integer of 0 to 2, which is transmitted to the ectoparasite by the animal's blood. In a further embodiment, a compound selected from the group consisting of ivermectin, milbemycin, milbemycin oxime, moxidectin and avermectin and avermectin derivatives.

35 Claims, No Drawings

U.S. PATENT DOCUMENTS

| | | | |
|---|---|---|---|
| 4,225,598 | 9/1980 | Brechbühler et al. | 514/245 |
| 4,321,388 | 3/1982 | Nishiyama et al. | 546/291 |
| 4,323,582 | 4/1982 | Siegel et al. | 514/667 |
| 4,346,171 | 8/1982 | Takiguchi et al. | 435/119 |
| 4,346,177 | 8/1982 | Cochet et al. | 501/123 |
| 4,350,706 | 9/1982 | Brouwer et al. | 514/594 |
| 4,399,152 | 8/1983 | Brouwer et al. | 514/594 |
| 4,405,552 | 9/1983 | Miesel | 514/348 |
| 4,473,582 | 9/1984 | Greene et al. | 514/531 |
| 4,540,578 | 9/1985 | Chou et al. | 514/349 |
| 4,547,520 | 10/1985 | Ide et al. | 514/450 |
| 4,677,127 | 6/1987 | Böger | 514/346 |
| 4,696,974 | 9/1987 | Sulc et al. | 525/926 |
| 4,751,223 | 6/1988 | Glamkowski et al. | 514/219 |
| 4,879,292 | 11/1989 | Nishida et al. | 514/241 |
| 4,970,222 | 11/1990 | Nishida et al. | 514/369 |
| 4,973,589 | 11/1990 | Barnett et al. | 514/245 |
| 4,988,824 | 1/1991 | Maulding et al. | 549/264 |

SYSTEMIC CONTROL OF PARASITES

REFERENCE TO RELATED APPLICATION

This is a divisional of application Ser. No. 08/210,135, filed on Mar. 17, 1994 now U.S. Pat. No. 5,439,924, which is a continuation of Ser. No. 07/980,591, filed on Nov. 23, 1992 (now abandoned), which is a continuation-in-part of Ser. No. 07/812,430, filed on Dec. 23, 1991 (now abandoned).

BACKGROUND OR THE INVENTION

1. Field of the Invention

The present invention relates to the use of certain nitrogen containing heterocyclics for systemic control of ectoparasites on homoiothermic or warm blooded animals and in another embodiment, the use of combinations of the nitrogen containing heterocyclics with other systemically active ingredients to control both ectoparasites and endoparasites.

2. Background of the Invention

Bloodsucking ectoparasites of the order Insecta include such as *Ctenocephalides felis* and *Ctenocephalides canis* (cat and dog fleas), as well as lice, mosquitos, tabanids, tsetse and other biting flies, and Acarina such as Boophilus, Amblyomma, Anocentor, Dermacentor, Haemaphysalis, Hyalomma, Ixodes, Rhipicentor, Margaropus, Rhipicephalus, Argas, Otobius and Ornithodoros (ticks), and the like, infest or attack many useful homoiothermic animals including farm animals such as cattle, swine, sheep, goat, poultry such as chicken, turkeys and geese, fur bearing animals such as mink, foxes, chinchilla, rabbits and the like, and pet animals such as dogs and cats.

Ticks are described as hard ticks or soft ticks and are characterized as one host, two host, or three host ticks. They attach to a suitable host animal and feed on blood and body fluids. Engorged females detach and drop from the host and lay large numbers of eggs (2,000 to 20,000) in a suitable niche in the ground or in some other sheltered location in which hatching occurs. The larva then seek a host from which to obtain a blood meal. Larvae of one host ticks molt on the host twice to become nymphs and adults without leaving the host. Larvae of two and three host ticks drop off the host, molt in the environment and find a second or third host (as nymph or adult) on which to feed.

Ticks are responsible for the transmission and propagation of many human and animal diseases throughout the world. Ticks of major economic importance include Boophilus, Rhipicephalus, Ixodes, Hyalomma, Amblyomma, and Dermacentor. They are vectors of bacterial, viral, rickettsial and protozoal diseases, and cause tick paralysis and tick toxicosis. Even a single tick can cause paralysis consequent to injecting its saliva into its host in the feeding process. Tick-borne diseases are usually transmitted by multiple-host ticks. Such diseases, including Babesiosis, Anaplasmosis, Theileriosis and Heart Water are responsible for the death and/or debilitation of vast numbers of pet and food animals throughout the world. In many temperate countries, Ixodid ticks transmit the agent of a chronic, debilitating disease, Lyme disease, from wildlife to man. In addition to disease transmission, ticks are responsible for great economic losses in livestock production. Losses are attributable not only to death, but also to damage of hides, loss of growth, reduction in milk production, and reduced grade of meat. Although the debilitating effects of tick infestations on animals have been recognized for years and tremendous advances have been made in tick control programs, no entirely satisfactory methods for controlling or eradicating these parasites have been forthcoming, and ticks have often developed resistance to chemical toxicants and dependent control measures.

Infestation of pets by fleas has long been a nuisance to pet owners. Because fleas are able to survive and multiply under a wide range of environmental conditions, controlling flea infestation requires a multifaceted program that must be vigorously applied to achieve any measure of success. Adult fleas live in the coat of the cat or dog and feed on blood. Male and female fleas mate still in the animal's coat and the female flea lays her eggs. The eggs do not adhere to the fur, but fall off and are distributed to the animal's environment. By this mechanism, while the total environment of the pet animal is infested with flea eggs, infestation is greatest in locations where the pet spends most of its time. Eggs hatch to larvae in about two days. There are three larval stages, each lasting about three days. In the last stage, the larva spins a cocoon and transforms into a pupa. Under optimum conditions (i.e., 33° C. and 65% relative humidity), eggs develop through larvae to pupae in about 8–10 days. After a further period of approximately 8 days, the pupae develop into young adult fleas in the cocoon, still dispersed in the pet's environment. These pre-emerged adult fleas wait in their pupae until they sense, by carbon dioxide tension and/or vibrations, the presence of an animal host, and then emerge explosively and jump into the air and onto the passing host. Under suitable environmental conditions of temperature and humidity, unfed emerged fleas that fail to find a host can survive for some time in the environment, waiting for a suitable host. It takes at least three weeks for eggs to develop to pre-emerged adults, able to reinfest a host animal. However, the pre-emerged adults can remain viable in the cocoon for months, as long as one year. In addition, under sub-optimal temperature conditions, it can take 4–5 months for eggs to develop into pupae containing pre-emerged adults. Fleas require a blood meal in order to become sexually mature and able to reproduce. After their rust blood meal, they undergo a shift in metabolism such that they cannot survive for any time off the host. The blood must come from the correct animal and the female flea's appetite requires that it consumes as much as 5 times its body weight of blood each day. The long life cycle, and especially, the extended period of pre-emergence dormancy, has made flea control with compounds applied topically to pet animals difficult and not entirely satisfactory. Most topically applied active ingredients have a limited residual effect, thus reinfestation by newly-emerged adults from the pet's environment is a constant problem.

Infestation of dogs and cats with fleas has several undesirable effects for the animals and their owners. Such undesirable effects include local irritation and annoying itching, leading to scratching. A high proportion of pet animals, particularly dogs, become allergic to flea saliva, resulting in the chronic condition known as flea bite allergy (or flea allergy). This condition causes the animal to bite and scratch, leading to excoriation of the skin, secondary pyogenic infection, hair loss, and chronic severe inflammatory skin changes. Furthermore, most dogs and cats that are infested with fleas also become infected with *Dipylidium caninum*, the tapeworm transmitted by fleas.

In prolonged absence of a suitable animal, newly emerged fleas attack any mammal, including humans, although they am not capable of full reproductive potential if human blood is their sole source of nutrition. Even in the presence of the pet animal, the owner may be bitten by fleas. Some humans may suffer allergic skin diseases as a result of being bitten by dog and cat fleas.

3

Since, like most insects, fleas can adapt to survive exposure to normally toxic agents, and the tolerance of dogs and cats to chemical agents varies, it is desirable to have a multiplicity of agents and methods available for controlling fleas. Prior art methods have included numerous toxic agents such as organophosphates (e.g., chlorpyrifos), carbamates (e.g., Carbaryl), pyrethroids (e.g., natural pyrethrins and permethrin), and other topical insecticides formulated and designed to kill the adult flea after their application to the pet. Many of the effective residual action toxic agents against fleas, such as DDT, benzene hexachloride, and other chlorinated hydrocarbon insecticides, have been banned from most countries because of environmental persistence of residues and their effect on certain wildlife. Others have been banned because of long-term health risks, including risks of cancer to chronically exposed humans. In the United States, even currently approved and available toxic agents that are effective against fleas, some only briefly, are under scrutiny because of concerns for long-term health hazards to pets and to their owners. These considerations have limited utility of insecticidal and acaricidal toxic compounds for control of fleas and ticks on pet animals and of ectoparasites on animals in general.

In addition to numerous insecticidal compositions aimed at controlling ectoparasites, systemic agents directed against ectoparasites have been suggested. For example, U.S. Pat. Nos. 3,962,458 and 4,031,239 disclose the application of various cyclopropane carboxylate compounds (pyrethroids) for controlling ectoparasites by systemic treatment of warm blooded animals. U.S. Pat. No. 4,006,236 discloses the systemic use of substituted octahydrophenanthridines. U.S. Pat. No. 4,053,631 discloses the systemic control of ectoparasites with alpha-cyano-m-phenoxybenzylalpha-c1-c4 alkyl-2-naphthaleneacetates. U.S. Pat. No. 4,323,582 discloses the systemic use of lower alkanolamines to repel bloodsucking parasites.

U.S. Pat. Nos. 4,089,975 and 4,092,421 disclose the feed-through administration of certain nitrogen containing heterocyclics for the control of manure-breeding insects by orally administering an insecticidally effective amount of the compound to a warm blooded animal. These applications indicate a feed-through mechanism wherein the active compound is orally administered to the host animal, passes unmetabolized through its digestive system, and is excreted in an insecticidally active form. This mechanism implies poor absorption of these compounds and does not suggest that nitrogen containing heterocyclic compounds would pass into the bloodstream of the animal and circulate in an active form therein.

Using as systemic agents the classes of methoprene-like juvenile hormones, flea growth inhibiting benzoylurea derivatives, and flea growth inhibiting triazine derivatives is disclosed in U.S. Pat. No. 4,973,589. Ovicidal activity is demonstrated by certain triazine derivatives, as well as for benzoylurea derivatives in U.S. Pat. No. 4,973,589 but no examples are given for the juvenile hormone class. Ovicidal activity in a target species has been reported for the juvenile hormone type materials, but only when applied topically to the animal.

Due to the variability of toxic effects in various animal species, and the high dose rates required for systemic effects with many of the prior art compounds, it is desirable that additional alternative control agents be made available. Certain substituted heterocyclics of known insecticidal activity are disclosed in U.S. Pat. Nos. 4,970,222, 4,879,292 and 4,751,223. However, these juvenile hormone-like nitrogen containing heterocyclic compounds have not heretofore been suggested as systemically administered ovicidal agents wherein an ovicidally effective dose is administered to the target ectoparasite when it feeds on the blood of the treated animal.

In many areas of the world; the environmental conditions and methods of maintaining animal populations that favor multiplication and survival of ectoparasites, similarly encourage the proliferation and spread of endoparasites, both those with a free living life cycle (e.g., intestinal roundworm parasites of the order Nematoda) and those that depend on transmission by vectors (e.g., lung, lymphatic and blood vascular dwelling parasites of the same order). Examples of intestinal parasites that flourish in these favorable conditions are ascarids and hookworms of dogs and cats. Intestinal parasites of the same order are also a major problem for the food and recreational animal industry, parasiting cattle, sheep, swine and horses. An example of a vector transmitted internal parasitic nematode is heartworm of dogs and, to a lesser extent cats, transmitted by mosquitoes. Because of the requirements for similar environmental conditions and methods of animal management, it is extremely common for companion and economic animals to be at the same time exposed to and infected by endoparasites and infested by ectoparasites such as fleas, ticks, lice, mange mites, and biting flies, including the mosquito, which is the vector for a most important endoparasite, heartworm. There is consequently an overwhelming need for a convenient single method of treatment that would prevent and treat both endoparasite infections and ectoparasite infestations.

SUMMARY OF THE INVENTION

It has now been found that surprisingly, the juvenile hormone like class of heterocyclics disclosed in U.S. Pat. Nos. 4,970,222, 4,879,292 and 4,751,223, of the general formula:

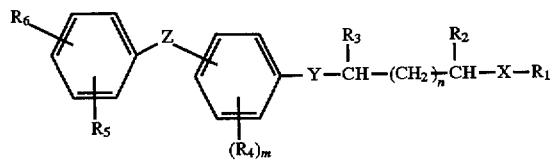

wherein $R_1$, is either one of the following groups:

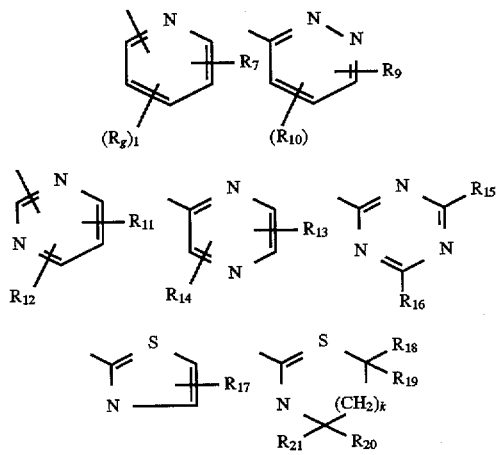

in which $R_7$, $R_8$, $R_9$, $R_{10}$, $R_{11}$, $R_{12}$, $R_{13}$, $R_{14}$, $R_{15}$, R16, and $R_{17}$ are, the same or different, each a hydrogen atom, a halogen atom, a $C_1$–$C_4$ alkoxy group, a $C_1$–$C_4$ alkylthio group, a trifluoro methyl group or a nitro group; $R_{18}$, $R_{19}$, $R_{20}$ and $R_{21}$ are, the same or different, each a hydrogen atom or a methyl group, k is an integer of 0 to 1 and l is an integer of 0 to 3; $R_2$ and $R_3$ are, the same or different, each a hydrogen atom, a halogen atom or a methyl group; $R_4$ is a halogen atom or a methyl group; $R_5$ and $R_6$ are, the same or different, each a hydrogen atom, a halogen atom, a $C_1$–$C_4$ haloalkyl group or a $C_1$–$C_4$ haloalkoxy group; X, Y and Z are, the same or different, each an oxygen atom, a sulfur atom or a methylene group, m is an integer of 0 to 4, and n is an integer of 0 to 2, including especially, pyriproxifen, 2-[1-methyl-2-(4-phenoxyphenoxy)ethoxy]pyridine (commercially available from the Sumitomo Chemical Company or from McLaughlin, Gormley, King Co. under the trademark NYLAR®), are effective systemically for controlling ectoparasites in homoiothermic (warm blooded) animals. When administered systemically in very low doses to test animals, the compounds demonstrate a powerful ovicidal effect toward ectoparasites. As used herein, the term ectoparasite has its normal meaning in the art and includes fleas, ticks, lice, mosquitos, tabanids, tsetse and other biting flies, and especially the species named above.

Systemically active compounds effective against several of these endoparasites include avermectins, avermectin-like derivatives and a group of related antibiotics, for instance milbemycin, milbemycin-like derivatives, ivermectin, ivermectin-like derivatives, milbemycin oxime, milbemycin oxime-like derivatives, moxidectin, moxidectin-like derivatives, and mixtures thereof, as disclosed by U.S. Pat. Nos. 4,346,177 and 3,950,360, (milbemycin), U.S. Pat. No. 4,199,569 (ivermectin), U.S. Pat. No. 4,547,520 (milbemycin oxime) and U.S. Pat. No. 4,988,824 and the copending applications incorporated therein (moxidectin).

Heartworm, ascarid and hookworm infections of dogs and cats can be prevented by administration of the antibiotic avermectin compounds by parenteral injection, oral dosage, transdermal application and by implanting solid or hollow devices designed to provide extended controlled release of the active compound. For instance, milbemycin, ivermectin, milbemycin oxime and moxidectin can be administered monthly to prevent and cure heartworm, hookworms and ascarids of dogs and cats.

A particularly convenient method of preventing infection and disease caused by these endoparasites, and in controlling ectoparasitic infestation, is the combination in a single product of a systemically active nitrogen containing heterocyclic compound of the invention as defined above and one of the compounds of the antibiotic class effective against endoparasites (e.g., including but not limited to milbemycin, ivermectin, milbemycin oxime and moxidectin). Administration of this convenient, effective and safe combination can be made by daily or periodic treatment (e.g., monthly) with liquid, chewable wafer or tablet oral dose forms, by parenteral injection, or by less frequent implantation of a controlled release device that contains and releases both a systemically active juvenile hormone-like nitrogen containing heterocyclic compound and a systemically active antibiotic effective against nematode parasites at rates that achieve and maintain blood levels adequate to affect the target endo- and ectoparasites.

DETAILED DESCRIPTION OF THE INVENTION

In the method of the present invention, ectoparasites are exposed to an ovicidally effective amount of the active ingredient when they ingest blood from an animal which has been treated with a systemically effective dose in a suitable carrier. The compounds may be administered in doses of about 0.0001 mg/kg to about 1000 mg/kg preferably about 0.01 mg/kg to about 100 mg/kg, more preferably about 0.01 mg/kg to about 70 mg/kg and most preferably about 0.02 to about 50 mg/kg. In an additional, preferred embodiment, the compounds in these amounts may be combined with endoparasitic control agents such as, for example, avermectin, avermectin-like derivatives, milbemycin, milbemycin derivatives, ivermectin, ivermectin derivatives, milbomycin oxime, milbemycin oxime derivatives, moxidectin, or moxidectin derivatives and mixtures thereof, in doses in the range of about 0.5 mcg/kg (micrograms per kilogram) to about 100 mg/kg. The preparation of ectoparasitic active compounds may be made by the methods described in any one of U.S. Pat. Nos. 4,920,222, 4,879,292, or 4,751,223. The disclosures of these patents are incorporated herein by reference. The endoparasitic control antibiotics can be prepared as described in U.S. Pat. Nos. 4,346, 171, 3,950,360, 4,199,569, 4,547,520 and 4,988,824 and copending applications incorporated therein by reference. The disclosures of these patents are incorporated herein by reference. The term "derivative" as used herein is intended to include compounds which exhibit endoparasitic control properties.

It is an essential feature of the present invention that the active compound is administered in such a manner that it can be ingested by the feeding parasite along with the blood of the host animal, and can then exhibit activity against the egg. As used herein, "host" means a host animal whose blood will permit an ectoparasite to achieve normal reproductive capabilities. As used herein, "ovicidally effective" means an effect which leads to a reduced rate of hatching of eggs or to the inability of the male to fertilize eggs, resulting in sterile egg production. In accordance with the present invention, this is achieved by several forms of application, for example, by administering a formulated active ingredient orally, parenterally, by implant, or as a bolus. In this case, the term "formulated" means in the form of a powder, a tablet, a wafer, a granulet, a capsule, an emulsion, a gel, a foam, or other compositions suitable for administering an effective amount of the active ingredient. The preparation does not necessarily have to be administered to the animal directly; it may be convenient to mix it with the animal's feed. In addition to containing adjuvants conventionally employed in the art of formulation, the compositions to be administered orally may of course contain further additives which stimulate voluntary ingestion by the animal, such as suitable scents or flavorings. Owing to its simplicity, oral application is one of the preferred modes of the present invention. A further mode of application is parenteral, for example, by subcutaneous, intravenous, or intramuscular injection, or by means of a sustained action preparation in the form of an implant, bolus, or other sustained release formulation. The application may be in a multiple dose or a single dose form.

Methods of oral application include, but are not limited to, compounds premixed in animal food, fed in biscuits or treats, chewable tablets or wafers, water dissolvable capsules or tablets, emulsifiable concentrates, water soluble compounds applied with a dropper into water, or materials applied in any form onto pet food. Implants may include any device applied to the animal for release of compounds to control ectoparasites. It is contemplated that the present invention may also be delivered to the animal by a transdermal transport system. Percutaneous administration is conveniently accomplished by subcutaneous, dermal, intramuscular, and even intravenous application of the injectable formulation. Conventional needle-type injection devices, as well as needleless air blast injection devices, as well as pour-on and spot-on formulations may be useful. It is possible to delay or sustain the permeation of the active ingredient through the animal's living tissues by proper formulation.

Sustained action of the active ingredient can be obtained by formulating the compound in a matrix that will physically inhibit dissolution. The formulated matrix is injected or otherwise surgically implanted into the body, where it remains as a depot from which the compound slowly dissolves, or in the case of hydrophobic compounds, is released by diffusion. Matrix formulations now known in the an are formulated in waxy semi-solids such as vegetable waxes and high molecular weight polyethylene glycols. Very effective sustained action is obtained by introducing into the animal an implant containing the active ingredient. Such implants are now well known in the veterinary art and are usually made of a silicon rubber or other polymerized plastic such as methacrylate. An especially useful implant composition is disclosed in U.S. Pat. No. 4,696,974. The active ingredient is dispersed through the solid implant or is contained inside a hollow implant. The active ingredient is dispersed by first dissolving or mixing with the polymer, or dissolved in, or mixed with a carrier, it is dispersed within the polymer. After implantation, the active ingredient diffuses or leaches out of the solid or hollow implant into the body fluids of the treated animal.

The rate at which the active ingredient is released from an implant, and hence, the length of time during which the implant remains effective, is controlled with good accuracy by the proper adjustment of the concentration of the compound in the implant, the external area of and amount of carrier in the implant, the external area of the implant, the formulation of the polymer from which the implant is made, the thickness of the wall of hollow implants and the diffusion characteristics of the active or carrier/active solution through the wall of the implant or through specially designed end-plugs of polymer or other membrane forming one or more surfaces of the implant, or by being forced through a porous membrane or aperture by an osmotic pump activated by absorption of body water into an osmotically active component contained in a second compartment of a hollow implant.

Administration of the active ingredient by means of an implant is a further particularly preferred embodiment. Such administration is highly economical and efficacious because a properly designed implant maintains a constant concentration of the compound in the tissues of the host animal, can be designed to supply a compound for several months, and is easily inserted in the animal. No further handling of the animal or concern over the dosage is necessary after implant insertion. Said implant may be erodible/soluble and may be left in the animal tissue, or it may be insoluble/non-erodible and suitable for surgical removal after exhaustion of its active ingredient.

A convenient bolus formulation is disclosed in U.S. Pat. No. 4,166,107 which may also be adopted for sustained release for the method of this invention.

The formulation of veterinary additives in animal feed is an extremely well known art. It is usual to formulate the compound first as a pre-mix in which the active ingredient is dispersed in a liquid or a particular solid carrier. The pre-mix may conveniently contain from about 1 to about 800 grams of compound per kilogram, depending on the desired concentration in the feed. To prevent hydrolysis or degradation by constituents of the animal feed, the active compound may be formulated in a protective matrix such as gelatin before addition to the pre-mix, and further protected by formulation with suitable preservatives, and antioxidants (e.g., sodium benzoate, parabens, BHT (butylated hydroxytoluene) and BHA (butylated hydroxyanisole).

The present invention is also directed to a method of systemically preventing the infestation of dogs and cats by fleas, which method comprises administering to said host animals orally, parenterally, or by implant an ovicidally effective amount of a compound of the formula:

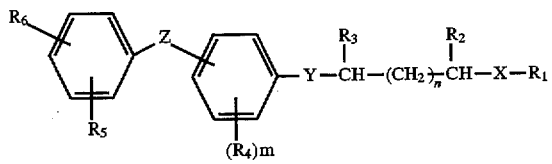

wherein $R_1$, is either one of the following groups:

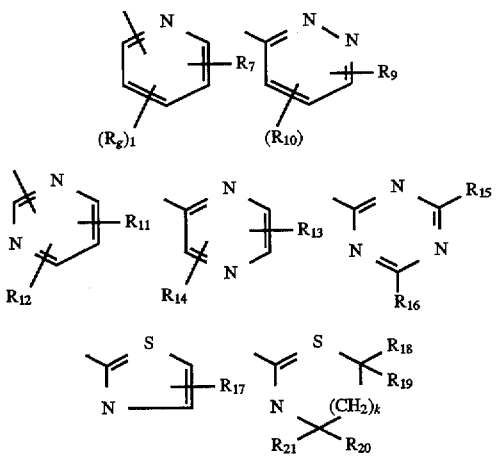

(in which $R_7$, $R_8$, $R_9$, $R_{10}$, $R_{11}$, $R_{12}$, $R_{13}$, $R_{14}$, $R_{15}$, $R_{16}$, and $R_{17}$ are, the same or different, each a hydrogen atom, a halogen atom, a $C_1$–$C_4$ alkoxy group, a $C_1$–$C_4$ alkythio group, a trifluoro methyl group or a nitro group; $R_{18}$, $R_{19}$, $R_{20}$ and $R_{21}$ are, the same or different, each a hydrogen atom or a methyl group, k is an integer of 0 to 1 and l is an integer of 0 to 3;) $R_2$ and $R_3$ are, the same or different, each a hydrogen atom, a halogen atom or a methyl group; $R_4$ is a halogen atom or a methyl group; $R_5$ and $R_6$ are, the same or different, each a hydrogen atom, a halogen atom, a $C_1$–$C_4$ haloalkyl group or a $C_1$–$C_4$ haloalkoxy group; X, Y and Z are, the same or different, each an oxygen atom, a sulfur atom or a methylene group, m is an integer of 0 to 4, and n is an integer of 0 to 2, which is transmitted to the ectoparasite by the animal's blood.

The present invention also relates to a method of preventing the propagation of fleas comprising the step of providing the fleas with nutrient blood, which contains an effective amount of active compound, and more specifically, the present invention relates to the method of preventing the propagation of fleas by feeding an effective amount of active compound to the host animal and letting the fleas feed thereon. The compound is conveniently applied orally in a dose of about 0.01 to about 200 mg/kg, preferably about 0.1 to about 100 mg/kg and most preferably about 0.1 to about 50 mg/kg body weight, based on the host animal. A good dose for regular administration is in general in the range of from about 0.2 to about 50 mg/kg body weight of the host animal. Doses are usefully regularly repeated at daily to monthly intervals. Large single doses may be effective for an even longer period. Such doses are preferably about 1 to about 1000 mg/kg, more preferably about 10–200 mg/kg, and most preferably about 20–100 mg/kg. The total dose of a particular active ingredient may vary from one genus of animal to another, and may even vary within the same genus since the preferred dose depends, among other things, on the weight and constitution of the animal.

In the method of the present invention, the active ingredient is not normally applied in pure form, but preferably in the form of a composition which, in addition to containing the active ingredient, contains application promoters which are tolerated by the host animal. Naturally, in addition to the method of controlling juvenile development stages in accordance with the present invention, the adult ectoparasites may also be controlled by conventional methods, particularly by topical application of insecticidal and acaricidal toxicants. However, these additional measures are not absolutely necessary. The composition to be applied by the method of this invention usually contains 0.1 to 99% by weight, preferably 0.1 to 95% by weight, of active compound and 99.9 to 1% by weight, preferably 99.9 to 5% by weight, of a solid or liquid non-toxic adjuvant, and may also incorporate preferably at least 0 to 25% by weight, 0.1 to 25% by weight of a non-toxic surfactant.

Commercial products may be formulated as concentrates, from which the end user will normally employ dilute formulations. The compositions may also contain further ingredients such as stabilizers, antioxidants, anti-foams, viscosity regulators, binders, tactifiers, preservatives, as well as other known and active ingredients for obtaining special effects. Materials known from veterinary practice as being suitable for being oral parenteral or implant administration may be employed as formulation assists. A number of examples are cited below.

Suitable carriers, especially fillers such as sugars, lactose, sucrose, mannitol or sorbitol, cellulose preparations, and/or calcium phosphates, for example, tricalcium phosphate or calcium hydrogen phosphate, also binders such as starch pastes, using, for example, corn, wheat, rice, or potato starch, gelatin, tragacanth, methylcellulose and/or if desired, disintegrators, such as the above-mentioned starches, also carboxymethyl starch, cross-linked to polyvinylpyrrolidone, agar, alginic acid, or a salt thereof, such as sodium alginate. Adjuvants are flow-regulating agents and lubricants, for example, silica, talc, stearic acid or salts thereof, such as magnesium stearate or calcium stearate, and/or polypropylene glycol. Dragée cores can be provided with suitable coatings that may be resistant to gastric juices, i.e., concentrated sugar solutions which may include gum arabic, talc, polyvinylpyrrolidone, polyethylene glycol and/or titanium dioxide, or lacquer in suitable organic solvents or solvent mixtures, or for the production of coatings that are resistant to gastric juices, solutions and suitable cellulose preparations, such as acetylcellulose phthalate, or hydroxypropylmethylcellulose phthalate may be used. Colorings, flavorings or pigments can be added to the tablets or Dragée coatings, for example, for identification purposes or to indicate different doses of active ingredients.

Further orally-administrable preparations are dry filled capsules consisting of gelatin and also soft-sealed capsules consisting of gelatin and applasticizers such as glycerol or sorbitol. The dry filled capsules may contain the active ingredient in the form of a granulate, for example, an admixture with fillers such as lactose, binders, such as starches, and glidants, such as talc or magnesium stearate, and optional stabilizers. In soft capsules, the active ingredient is preferably dissolved or suspended in suitable liquids, such as fatty oils, paraffin oils, or liquid polyethylene glycols, it being possible to also add stabilizers.

Especially suitable for parenteral administration are aqueous and oily solutions or suspensions of the active ingredient, such as an oily injection suspension, with a suitable lipophilic solvent or vehicle such as a fatty oil, for example, sesame oil, or synthetic fatty acid esters, for example, ethyloleate, or triglycerides, or aqueous injectable suspensions that contain viscosity increasing substances, for example, sodium carboxymethylcellulose, sorbitol and/or dextran, and, optionally also stabilizers. The preparations useful for the present invention can be manufactured by conventional methods, such as, for example, mixing, granulating, confectioning, dissolving or lyophilizing processes. For example, pharmaceutical preparations for oral administration can be obtained by combining the active ingredient with solid carriers, optionally granulating a resultant mixture, and processing the mixture of granulate, if desired or necessary, after the addition of suitable adjuncts, to form tablets or Dragée cores.

In an alternative embodiment, combinations of systemic endoparasite control agents are combined with the nitrogen containing heterocyclics of the present invention to produce novel multifunction parasite control compositions. The endoparasite control agents include the avermectins and their derivatives, preferably milbemycin, ivermectin, milbemycin oxime or moxidectin in a parasiticidally effective dose. The effective dose will be in the range of about 0.01 to about 100 mg/kg, preferably about 0.1 to about 50 mg/kg for milbemycin; about 0.01 to about 10 mg/kg, preferably about 0.025 to about 0.5 mg/kg for ivermectin, about 0.01 to about 100 mg/kg preferably about 0.5 to about 50 mg/kg for milbemycin oximes and about 0.5 to about 100 mcg/kg, preferably about 1.25 to about 50 mcg/kg for moxidectin. Especially preferred combinations are an ectoparasiticidally effective amount of pyriproxifen in combination with endectocidally effective amount of a compound selected from the group consisting of milbemycin, milbemycin derivatives, ivermectin, ivermectin derivatives, milbemycin oxime, milbemycin oxime derivatives, moxidectin, and moxidectin derivatives, or mixtures thereof. An especially preferred composition comprises an ectoparasiticidally effective amount of pyriproxifen, an endectocidally effective amount of moxidectin and a pharmaceutically acceptable carrier.

In another preferred embodiment the method of the present invention comprises administering to a warm blooded animal a composition comprising an ovicidally effective amount of pyriproxifen in combination with a parasiticidally effective amount of a macrocyclic ester selected from the group comprising avermectin, milbemycin, milbemycin oxime, ivermectin and moxidectin, such that the active ingredients are transmitted to target parasites via the blood of the warm blooded animal in parasiticidally effective amounts sufficient to protect the animal from ectoparasites and endoparasites.

A preferred embodiment of the method of the present invention comprises the steps of administering a parasiticidally effective dose comprising a mixture of from about 0.001 to about 200 mg/kg of pyriproxifen and about 0.5 to about 100 mcg/kg of moxidectin to a warm-blooded animal, preferably a dog, cat, cow, sheep, goat, pig, mink, fox, rabbit, chicken, duck or goose. The compositions comprising the nitrogen containing heterocyclic systemic ovicides and avermectin derivatives of the present invention, especially the preferred composition of the combination of about 0.2 to about 100 mg/kg pyriproxifen with about 1.25 to about 50 mcg/kg moxidectin and the method of administering the composition of about 0.2 to about 50 mg/kg pyriproxifen and about 1.25 to about 50 mcg/kg of moxidectin to a warm-blooded animal, such that parasiticidally effective amounts of the active ingredients are transmitted to the ectoparasites or endoparasites via the blood of the warm-blooded animal are especially preferred embodiments of the present invention.

It is expected that when compositions of the preferred combinations as formulated in examples 11 and 12 below are administered to dogs infested with fleas that are maintained in an environment favorable to development of larvae, their pupation and the emergence of new fleas to reinfest the dogs, the dogs are also continually exposed to heartworm infection through the biting of mosquitos transmitting infective larvae of *D. immitis* and the dogs are observed for 6 months, that the test animals will be substantially free of both fleas and heartworms at the end of the test period, while similarly maintained control dogs will suffer severe and increasing infestations of both fleas and heartworms. It is also expected that the ecto and endoparasiticidal compositions will show a broad protection against fleas, ticks, mosquitoes, lice, mange mites, and biting flies as well as anthelminitic and antiparasitic effects against the metazoan parasites known as Helminthes, especially Nematoda and members of the family Filaridae or Setariidae, and the genera Dirofilaria in dogs and Nematospiroides, Syphacia and Aspiculuris in the rhodentias. It is anticipated that combinations of pyriproxifen with milbemycin, ivermectin, milbemycin oxime or moxidectin may also exhibit enhanced or synergistic effects wherein one or more components of the mixtures is more efficacious than the same dose administered alone. The following examples illustrate the invention described herein, but do not limit its scope in any way.

EXAMPLE 1

Tablets (1000)

Tablets containing 25 mg of active ingredient, for example, 2-[1-methyl-2-(4-phenoxyphenoxy)ethoxy] pyridine (pyriproxifen), can be manufactured as follows:

| CONSTITUENTS | AMOUNT |
| --- | --- |
| Active ingredient | 25 g |
| Lactose | 100.7 g |
| Wheat starch | 7.5 g |
| Polyethylene glycol (mol. wt. 6,000) | 5.0 g |
| Talc | 5.0 g |
| Magnesium stearate | 1.8 g |
| Demineralized water | q.s. |

All of the solid ingredients are first forced through a sieve having a mesh of 0.6 mm., then the active ingredient, the lactose, the talc, the magnesium stearate, and half the starch, are mixed. The other half of the starch is suspended in 40 ml. of water and the suspension is added to a boiling solution of the polyethylene glycol in 100 ml. of water. The resulting starch base is added to the main batch and the mixture, if necessary, with the addition of water, is granulated. The granulate is dried overnight at 35° C., forced through a sieve having a mesh width of 1.2 mm. and pressed to form tablets.

EXAMPLE 2

Tablets

Tablets containing 20 mg of active ingredient, for example, 2-[1-methyl-2-(4-phenoxyphenoxy)ethoxy] pyridine pyriproxifen, can be manufactured as follows:

| COMPOSITION | AMOUNT |
| --- | --- |
| Active ingredient | 200.0 g |
| Lactose | 290.8 g |
| Potato starch | 274.7 g |
| Stearic acid | 10.0 g |
| Talc | 200.0 g |
| Magnesium stearate | 2.5 g |
| Colloidal silica | 30.0 g |
| Ethanol | q.s. |

The mixture of the active ingredient, the lactose and 194.70 g of potato starch, is moistened with an ethanolic solution of the stearic acid and granulated through a sieve. After drying the remainder of the potato starch, talc, magnesium stearate, and colloidal silica are added mixed to the mixtures and pressed to form 0.1 g tablets which, if desired, can be provided with breaking grooves for finer adjustment of the dosage.

EXAMPLE 3

Capsules

Capsules containing 25 mg of active ingredient, for example, 2-[1-methyl-2-(4-phenoxyphenoxy)ethoxy] pyridine, can be manufactured as follows:

| COMPOSITION | AMOUNT |
| --- | --- |
| Active ingredient | 25.0 g |
| Lactose | 249.0 g |
| Gelatin | 2.0 g |
| Corn starch | 10.0 g |
| Talc | 15.0 g |
| Water | q.s. |

The active ingredient is mixed with the lactose and the mixture is moistened uniformly with an aqueous solution of the gelatin and granulated through a sieve having a mesh width of 1.2–1.5 mm. The granulate is then mixed with the dried cornstarch and the talc and introduced in portions of 300 mg into hard gelatin capsules (size 1).

EXAMPLE 4

Pre-mix (feed additive)

0.25 parts by weight of active ingredient, for example, pyriproxifen, and 4.75 parts of secondary calcium phosphate, or China clay, aerosil or carbonate or lime or homogeneously mixed with 95 parts of an animal feed.

EXAMPLE 5

Emulsifiable concentrate 20 parts of active ingredient, for example, pyriproxifen, are mixed with:

20 parts of emulsifier (e.g., a mixture of alkylarylpolyglycol ether with alkylarylsulphonates), and 60 parts of solvent until the solution is completely homogenous. By diluting this concentrate with water, it is possible to obtain an emulsion of the desired concentration.

EXAMPLE 6

Soluble powder 25 parts of active ingredient, for example, pyriproxifen;

1 part sodium lauryl sulfate;

3 parts colloidal silica; and 71 parts urea.

The constituents are mixed and the mixture is finally ground in a suitable mill.

EXAMPLE 7

Gels

| COMPOSITION | AMOUNT (g) |
| --- | --- |
| Active ingredient | 0.5 |
| Cod Liver Oil | 12.5 |
| Corn Oil | 124.5 |
| Beef Peptone | 2.5 |
| Molasses | 5.0 |
| Glucose | 12.5 |
| Sodium Benzoate | 5.0 |
| Methyl Cellulose | 12.5 |
| Demineralized Water | 75.0 |

The active ingredient, for example, pyriproxifen, is dissolved in the oil phase. Glucose, peptone, sodium benzoate and molasses are dissolved in the demineralized water heated to 60° C. into which the methylcellulose is blended to form a gel, which is then blended with the oil phase. The gel is filled into flexible plastic squeeze tubes which are crimp sealed and capped. Alternatively, the gel may be filled into "dial-a-dose" syringes graduated to supply the desired daily dose rate/lb body weight, for instance 1 g/10 kg body weight. This basic daily oral dose form gel may be improved by addition of vitamins (e.g., A, D, E and the B group), minerals, trace elements and essential fatty acids, to provide an easy-to-administer, complete nutritional supplement for pet animals that also provides effective ectoparasite control. The proportions of ingredients set out above provide 2.0 mg of active ingredient per gram of gel.

EXAMPLE 8

Dietary supplement

| COMPOSITION | AMOUNT (g) |
| --- | --- |
| Active ingredient | 1.0 |
| Fish Oil (Omega 3) | 80.0 |
| Borage Seed Oil (gamma linolenic acid) | 20.0 |
| Sunflower Seed Oil | 847.9 |
| Chicken Flavor | 5.0 |
| Butylated Hydroxytoluene | 1.0 |
| Propylene Glycol | 20.0 |
| Zinc Sulphate | 1.0 |
| Tocopherol Acetate | 3.0 |
| Inositol | 0.5 |
| Pyridoxine Hydrochloride | 0.1 |
| Vitauiin A Palmitate | 0.1 |
| Biotin | 0.1 |
| Propyl-Methyl Parabens | 0.3 |

All ingredients are dissolved/blended in the oil phase. The liquid supplement is filled into flexible plastic squeeze "tip-and-measure," liter bottles which are capped. Daily dosage as a liquid food additive for dogs and cats is as appropriate to body weight and desired daily dose rate (mg active/kg body weight, or oz/25 lb body weight). Administration of dermatologically-active essential fatty acid/vitamin/zinc supplements are especially beneficial for pet animals suffering from dermatitis caused by exposure to infestations of ectoparasites. The proportions of ingredients set out above provides, 1 mg active ingredient for example, pyriproxifen, per gram of dietary supplement.

EXAMPLE 9

Monolithic 150 mg Implant

| COMPOSITION | AMOUNT (mg) |
| --- | --- |
| Active ingredient | 30.0 |
| Methacrylate hydrophilic polymer | 30.0 |
| Elastomeric silicone composite | 90.0 |

The active ingredient, for example pyriproxifen, is mixed with the prepared hydrophilic copolymer powder to which is added the silicone composite, for instance hydroxy-hydrogen-poly (dimethylsiloxane) and methyltriacetoxysiloxane cross linking agent in the proportions shown. The mixture is reacted at ambient temperature in a mold for 12 hours. Implants are sterilized by gamma radiation or by gassing with ethylene oxide after packaging. Implants are inserted subcutaneously either by trochar or by minor surgical procedure. Multiple implants may be inserted simultaneously depending on the animal's weight, on the known release rate of active ingredient and on the desired frequency of replantation. The example single implant provides adequate blood levels for 90 days to sterilize all eggs laid by female fleas feeding on an implanted cat weighing 3 kg.

EXAMPLE 10

Transdermal Gel

| COMPOSITION | AMOUNT (g) |
| --- | --- |
| Active ingredient | 12.5 |
| Corn Oil | 12.5 |
| Dimethylsuffoxide | 12.5 |
| Butylated Hydroxytoluene | 1.3 |
| Methyl Cellulose | 5.0 |
| Demineralized Water | 206.3 |

The active ingredient is dissolved in the oil phase to which the other excipients are added and the mixture blended to a smooth gel of viscosity 1000–1200 centipoise. The gel is filled in 2 ml aliquots into unit dose flexible plastic squeeze tubes which are heat sealed. Alternatively, the gel may be filled into "dial-a-dose," multi-dose syringes graduated and adjustable to supply, at the appropriate dose rate, the desired monthly dose, for topical application directly on to the skin of the animal's back. The proportions of ingredients set out above provides 50 mg of active ingredient per gram of transdermal gel.

Other biocidally-active ingredients or agents which are inert towards the active ingredients and acceptable to the animals to be treated or mineral salts or vitamins can be admixed with the compositions above described. In a manner analogous to that described in the formulation Examples 1 to 10, it is possible to manufacture corresponding preparations containing any compound selected from the group of nitrogen containing heterocyclic compounds as defined above. Preferred compounds are those wherein $R_1$ is a 2-substituted pyridine, a pyrimidine or a 1,3 thiazol; especially preferred compounds are 2(4-phenoxyphenoxy) ethoxy substituted pyridines, and most preferred is the compound 2-[1-methyl-2-(4-phenoxyphenoxy)ethoxy] pyridine. Alternatively the nitrogen containing heterocyclics may be combined with an avermectin antibiotic as described below.

EXAMPLE 11

Flea control through the oral administration of an active ingredient

Technical grade pyriproxifen, 2-[-1-methyl-2-(4-phenoxyphenoxy)ethoxy]pyridine, was diluted in corn oil and filled into gelatin capsules. The active ingredient loads were designed to provide nominal doses of 0.2, 2.0, and 20 milligrams (mg) per kilogram (kg) body weight for each of 6 cats, grouped in pairs. The test subjects were good flea hosts, docile and amenable to daily oral pilling. The cats were individually caged with flea egg collectors, water and food ad-lib., two additional cats were maintained in the same fashion as controls. The egg production was monitored by 2 collections prior to treatment of the animals. Doses of the active compounds were given on day 5, days 11–15, and days 18–22 of a 28-day test period. The flea eggs were collected and cultured on a suitable larvae rearing medium. The hatching rate and the adult flea emergent rates were measured. The active ingredient was administered as a corn oil capsule. The number of pupae and adult fleas which hatched was determined (Tables 1 and 2).

The data shows partial or complete sterilization of flea eggs at all doses, as measured by hatch and larvae counts or by full development and adult emergence. The sterilizing effect, whether measured by egg hatch-larvae counts or by adult flea emergent, were essentially similar, except that the apparent fertility of eggs collected before the first dose and from control counts throughout showed higher fertility based on larvae counts compared with fertility based on adult flea emergence. Complete sterility of the flea eggs from day 14 on at all dose levels was observed. At doses of 2 mg/kg and 20 mg/kg, complete egg sterilization was seen by day 12. In this manner the life cycle of the flea is broken and flea control is achieved.

TABLE 1

Pyriproxifen Oral - Systemic Ovicidal Effect on Flea Eggs
Post-treatment Flea Egg Fertility
Larval hatch from 25 flea eggs

| | | Days after Treatment | | | | | | | |
|---|---|---|---|---|---|---|---|---|---|
| | | 5 | | 12 | | 14 | | 20 | |
| Cat No. | Dosage mg/kg | No. Larvae | % | No. Larvae | % | No. Larvae | % | No. Larvae | % |
| 904 | 0.17 | 22 | 88.0% | 2 | 8.0% | 0 | 0.0% | 0 | 0.0% |
| 1264 | 0.22 | 21 | 84.0% | 2 | 8.0% | 0 | 0.0% | 0 | 0.0% |
| 1217 | 2.34 | 20 | 80.0% | 0 | 0.0% | 0 | 0.0% | 0 | 0.0% |
| 3179 | 2.14 | 21 | 84.0% | 0 | 0.0% | 0 | 0.0% | 0 | 0.0% |
| 3183 | 20.30 | 23 | 92.0% | 0 | 0.0% | 0 | 0.0% | * | |
| 1265 | 19.52 | 21 | 84.0% | 0 | 0.0% | 0 | 0.0% | 0 | 0.0% |
| 3185 | — | 18 | 72.0% | 12 | 48.0% | 8 | 32.0% | 18 | 72.0% |
| 3186 | — | 22 | 88.0% | 13 | 52.0% | 14 | 56.0% | 24 | 96.0% |
| Mean Controls | | 20 | 80.0% | 13 | 50.0% | 11 | 44.0% | 21 | 84.0% |
| Mean Treated | | | | | | | | | |
| @ 0.17–0.18 mg/kg | | 22 | 86.0% | 2 | 8.0% | 0 | 0.0% | 0 | 0.0% |
| @ 2.14–2.34 mg/kg | | 21 | 82.0% | 0 | 0.0% | 0 | 0.0% | 0 | 0.0% |
| @ 19.52–20.30 mg/kg | | 22 | 88.0% | 0 | 0.0% | 0 | 0.0% | 0 | 0.0% |
| Efficacy | | | | | | | | | |
| @ 0.17–0.18 mg/kg | | | −8% | | 84% | | 100% | | 100% |
| @ 2.14–2.34 mg/kg | | | −3% | | 100% | | 100% | | 100% |
| @ 19.52–20.34 mg/kg | | | −10% | | 100% | | 100% | | 100% |

*Failed to collect eggs from 3183 on day 20.

TABLE 2

Pyriproxifen Oral - Systemic Ovicidal Effect
Adult flea emergence from 50 flea eggs cultivated each test

| Cat No. | Dosage mg/kg | No. Fleas | % | No. Fleas | % | No. Fleas | % | No. Fleas | % | No. Fleas | % | No. Fleas | % | No. Fleas | % |
|---|---|---|---|---|---|---|---|---|---|---|---|---|---|---|---|
| | | | | | | | | Day of Test | | | | | | | |
| | | 4 | | 5 | | 8 | | 11 | | 12 | | 13 | | 14 | |
| | | | | | | | | Days Treated | | | | | | | |
| | | | | * | | | | * | | * | | * | | * | |
| 904 | 0.17 | 43 | 86.0% | 36 | 72.0% | 4 | 8.0% | 13 | 26.0% | 4 | 8.0% | 0 | 0.0% | 0 | 0.0% |
| 1264 | 0.18 | 33 | 66.0% | 36 | 72.0% | 13 | 26.0% | 19 | 38.0% | 3 | 6.0% | 0 | 0.0% | 0 | 0.0% |

TABLE 2-continued

Pyriproxifen Oral - Systemic Ovicidal Effect
Adult flea emergence from 50 flea eggs cultivated each test

| Cat No. | Dosage mg/kg | No. Fleas | % | No. Fleas | % | No. Fleas | % | No. Fleas | % | No. Fleas | % | No. Fleas | % | No. Fleas | % |
|---|---|---|---|---|---|---|---|---|---|---|---|---|---|---|---|
| 1217 | 2.34 | 37 | 74.0% | 17 | 34.0% | 0 | 0.0% | 0 | 0.0% | 0 | 0.0% | 0 | 0.0% | 0 | 0.0% |
| 3179 | 2.14 | 38 | 76.0% | 18 | 36.0% | 0 | 0.0% | 0 | 0.0% | 1 | 2.0% | 0 | 0.0% | 0 | 0.0% |
| 3183 | 20.30 | 31 | 62.0% | 43 | 86.0% | 0 | 0.0% | 0 | 0.0% | 0 | 0.0% | 0 | 0.0% | 0 | 0.0% |
| 1265 | 19.52 | 43 | 86.0% | 13 | 26.0% | 0 | 0.0% | 0 | 0.0% | 0 | 0.0% | 0 | 0.0% | 0 | 0.0% |
| 3186 | — | 33 | 66.0% | 28 | 56.0% | 31 | 62.0% | 28 | 56.0% | 29 | 58.0% | 3 | 6.0% | 17 | 34.0% |
| 3185 | — | 31 | 62.0% | 28 | 56.0% | 16 | 32.0% | 15 | 30.0% | 31 | 62.0% | 9 | 18.0% | 6 | 12.0% |
| Mean Controls | | 32 | 64.0% | 28 | 56.0% | 24 | 47.0% | 22 | 43.0% | 30 | 60.0% | 6 | 12.0% | 12 | 23.0% |
| Mean Treated | | | | | | | | | | | | | | | |
| @ 0.17–0.18 mg/kg | | 38 | 76.0% | 36 | 72.0% | 9 | 17.0% | 16 | 32.0% | 4 | 7.0% | 0 | 0.0% | 0 | 0.0% |
| @ 2.14–2.34 mg/kg | | 38 | 75.0% | 18 | 35.0% | 0 | 0.0% | 0 | 0.0% | 1 | 1.0% | 0 | 0.0% | 0 | 0.0% |
| @ 19.52–20.30 mg/kg | | 37 | 74.0% | 28 | 56.0% | 0 | 0.0% | 0 | 0.0% | 0 | 0.0% | 0 | 0.0% | 0 | 0.0% |
| Efficacy | | | | | | | | | | | | | | | |
| @ 0.17–0.18 mg/kg | | | −19% | | −29% | | 64% | | 26% | | 88% | | 100% | | 100% |
| @ 2.14–2.34 mg/kg | | | −17% | | 38% | | 100% | | 100% | | 98% | | 100% | | 100% |
| @ 19.52–20.34 mg/kg | | | −16% | | 0% | | 100% | | 100% | | 100% | | 100% | | 100% |

| | | Day of Test | | | | | | | | | | | | | |
|---|---|---|---|---|---|---|---|---|---|---|---|---|---|---|---|
| | | 15 | | 18 | | 19 | | 20 | | 21 | | 22 | | 26 | |
| | | Days Treated | | | | | | | | | | | | | |
| | | * | | * | | * | | * | | * | | * | | | |
| 904 | 0.17 | 0 | 0.0% | 0 | 0.0% | 0 | 0.0% | 0 | 0.0% | 0 | 0.0% | 0 | 0.0% | 3 | 6.0% |
| 1264 | 0.18 | 0 | 0.0% | 0 | 0.0% | 0 | 0.0% | 0 | 0.0% | 0 | 0.0% | 0 | 0.0% | 0 | 0.0% |
| 1217 | 2.34 | 0 | 0.0% | 0 | 0.0% | 0 | 0.0% | 0 | 0.0% | 0 | 0.0% | 0 | 0.0% | 0 | 0.0% |
| 3179 | 2.14 | 0 | 0.0% | 0 | 0.0% | 0 | 0.0% | 0 | 0.0% | 0 | 0.0% | 0 | 0.0% | 0 | 0.0% |
| 3183 | 20.30 | 0 | 0.0% | 0 | 0.0% | 0 | 0.0% | 0 | 0.0% | 0 | 0.0% | 1 | 2.0% | 0 | 0.0% |
| 1265 | 19.52 | 0 | 0.0% | 0 | 0.0% | 0 | 0.0% | 0 | 0.0% | 0 | 0.0% | 0 | 0.0% | 0 | 0.0% |
| 3186 | — | 18 | 36.0% | 12 | 24.0% | 21 | 42.0% | 32 | 64.0% | 29 | 58.0% | 34 | 68.0% | 20 | 40.0% |
| 3185 | — | 4 | 8.0% | 18 | 36.0% | 18 | 36.0% | 28 | 56.0% | 37 | 74.0% | 21 | 42.0% | 28 | 56.0% |
| Mean Controls | | 11 | 22.0% | 15 | 30.0% | 20 | 39.0% | 30 | 60.0% | 33 | 66.0% | 28 | 55.0% | 24 | 48.0% |
| Mean Treated | | | | | | | | | | | | | | | |
| @ 0.17–0.18 mg/kg | | 0 | 0.0% | 0 | 0.0% | 0 | 0.0% | 0 | 0.0% | 0 | 0.0% | 0 | 0.0% | 2 | 3.0% |
| @ 2.14–2.34 mg/kg | | 0 | 0.0% | 0 | 0.0% | 0 | 0.0% | 0 | 0.0% | 0 | 0.0% | 0 | 0.0% | 0 | 0.0% |
| @ 19.52–20.30 mg/kg | | 0 | 0.0% | 0 | 0.0% | 0 | 0.0% | 0 | 0.0% | 0 | 0.0% | 1 | 1.0% | 0 | 0.0% |
| Efficacy | | | | | | | | | | | | | | | |
| @ 0.17–0.18 mg/kg | | | 100% | | 100% | | 100% | | 100% | | 100% | | 100% | | 94% |
| @ 2.14–2.34 mg/kg | | | 100% | | 100% | | 100% | | 100% | | 100% | | 100% | | 100% |
| @ 19.52–20.34 mg/kg | | | 100% | | 100% | | 100% | | 100% | | 100% | | 98% | | 100% |

Effective control of Acarina was demonstrated in U.S. Pat. Nos. 4,920,222; 4,879,292; and 4,251,223 with female carmine spider mites. The data of the present invention indicate that surprisingly the compounds of the invention will provide systemic control of Acarina ectoparasites via the blood of treated host animals.

Comparable results to those in example 11 will be obtained when formulations of examples 1 to 10 are administered to test animals with the other compounds described above for the invention as active ingredients. Systemic ovicidal activity against other ectoparasites for the active compounds identified above will be observed when the test compound is administered as in Example 9 and the ectoparasites are allowed to feed on the test animal, even where the test animal is a host for the particular species.

EXAMPLE 12

Flea control through single-dose oral administration of an active ingredient

Pyriproxifen was administered to 6 cats essentially as described in Example 11, with the exception that a single dose of pyriproxifen (about 2.0, 20.0 or 50.0 mg/kg) or placebo (corn oil in gelatin capsules) was administered in lieu of multiple dose treatment. The number of pupae and adult fleas which hatched was determined (Table 3 and 4). The results demonstrate a dose-response relationship in after-treatment egg hatch. The reoccurrence of fertile eggs was earliest at the lowest dose rate (2 mg/kg at day 9) while the longest interval before fertile egg reoccurrence was observed with the highest dose (50 mg/kg on day 25).

Adult flea emergence was similar (Table 4). A 2 mg/kg single dose prevented emergence before the 7th day after treatment, 20 mg/kg was effective until 17 or 29 days, and 50 mg/kg was effective until 25 or 28 days.

TABLE 3

Pyriproxifen Oral - Single Dose Residual Ovicidal Effect on Flea Eggs
Post-treatment Flea Egg Fertility
Larval Hatch from 25 eggs

| Cat no. | Dosage mg/kg | No. Larvae | % | No. Larvae | % | No. Larvae | % | No. Larvae | % | No. Larvae | % |
|---|---|---|---|---|---|---|---|---|---|---|---|
| | | \multicolumn{10}{c}{Day Reinfested} |
| | | 0 | | 2 | | 4 | | 7 | | 9 | |
| 915 | 0.0 | 21 | 84.0% | 23 | 92.0% | 23 | 92.0% | 16 | 64.0% | 23 | 92.0% |
| 3162 | 0.0 | 16 | 64.0% | 22 | 88.0% | 25 | 100% | 22 | 88.0% | 24 | 96.0% |
| 1203 | 2.0 | 0 | 0.0% | 0 | 0.0% | 23 | 92.0% | 17 | 68.0% | \multicolumn{2}{c}{Terminated} |
| 1267 | 2.1 | 0 | 0.0% | 0 | 0.0% | 9 | 36.0% | 8 | 32.0% | \multicolumn{2}{c}{Terminated} |
| 1218 | 21.2 | 0 | 0.0% | 0 | 0.0% | 0 | 0.0% | 0 | 0.0% | 0 | 0.0% |
| 3325 | 22.1 | 0 | 0.0% | 0 | 0.0% | 0 | 0.0% | 0 | 0.0% | 0 | 0.0% |
| 3164 | 54.3 | 0 | 0.0% | 0 | 0.0% | 0 | 0.0% | 0 | 0.0% | 0 | 0.0% |
| 3404 | 53.1 | 0 | 0.0% | 0 | 0.0% | 0 | 0.0% | 0 | 0.0% | 0 | 0.0% |
| Mean Control | | 19 | 74.0% | 23 | 90.0% | 24 | 96.0% | 19 | 76.0% | 24 | 94.0% |
| Mean Treated | | | | | | | | | | | |
| @ 2 mg/kg | | 0 | 0.0% | 0 | 0.0% | 16 | 46.0% | 13 | 34.0% | | |
| @ 21.5 mg/kg | | 0 | 0.0% | 0 | 0.0% | 0 | 0.0% | 0 | 0.0% | 0 | 0.0% |
| @ 53.7 mg/kg | | 0 | 0.0% | 0 | 0.0% | 0 | 0.0% | 0 | 0.0% | 0 | 0.0% |
| Efficacy | | | | | | | | | | | |
| @ 2 mg/kg | | | 100% | | 100% | | 33% | | 34% | | |
| @ 21.5 mg/kg | | | 100% | | 100% | | 100% | | 100% | | 100% |
| @ 53.7 mg/kg | | | 100% | | 100% | | 100% | | 100% | | 100% |

(Table continued — columns for Days 11, 14, 16 in upper block, and 18, 21, 23, 25, 28, 30, 32 in lower block)

| Cat no. | Dosage mg/kg | No. Larvae (18) | % | No. Larvae (21) | % | No. Larvae (23) | % | No. Larvae (25) | % | No. Larvae (28) | % | No. Larvae (30) | % | No. Larvae (32) | % |
|---|---|---|---|---|---|---|---|---|---|---|---|---|---|---|---|
| 915 | 0.0 | 21 | 84.0% | 23 | 92.0% | | | 21 | 84.0% | 17 | 68.0% | | | 20 | 80.0% |
| 3162 | 0.0 | 19 | 76.0% | 22 | 88.0% | | | 18 | 72.0% | 20 | 80.0% | | | 20 | 80.0% |
| 1203 | 2.0 | | | | | | | | | | | | | | |
| 1267 | 2.1 | | | | | | | | | | | | | | |
| 1218 | 21.2 | 2 | 8.0% | 9 | 36.0% | \multicolumn{2}{c}{Terminated} | | | | | | | | |
| 3325 | 22.1 | 0 | 0.0% | 0 | 0.0% | | | 0 | 0.0% | 2 | 8.0% | | | 6 | 24.0% |
| 3164 | 54.3 | 0 | 0.0% | 0 | 0.0% | | | 1 | 4.0% | 6 | 24.0% | \multicolumn{2}{c}{Terminated} | | |
| 3404 | 53.1 | 0 | 0.0% | 0 | 0.0% | | | 2 | 8.0% | \multicolumn{2}{c}{Terminated} | | | | |
| Mean Control | | 20 | 80.0% | 23 | 90.0% | | | 20 | 78.0% | 19 | 74.0% | | | 20 | 80.0% |
| Mean Treated | | | | | | | | | | | | | | | |
| @ 2 mg/kg | | | | | | | | | | | | | | | |
| @ 21.5 mg/kg | | 1 | 4.0% | 5 | 18.0% | | | 0 | 0.0% | 2 | 8.0% | | | 6 | 24.0% |
| @ 53.7 mg/kg | | 0 | 0.0% | 0 | 0.0% | | | 2 | 6.0% | 6 | 12.0% | | | | |
| Efficacy | | | | | | | | | | | | | | | |
| @ 2 mg/kg | | | | | | | | | | | | | | | |
| @ 21.5 mg/kg | | | 95% | | 80% | | | | 100% | | 89% | | | | 70% |
| @ 53.7 mg/kg | | | 100% | | 100% | | | | 92% | | 68% | | | | |

TABLE 4

Pyriproxifen Oral - Single Dose Residual Ovicidal Effect on Flea Eggs
Adult flea emergence from 50 flea eggs cultivated each test

| Cat No. | Dosage mg/kg | No. Fleas | % Fleas | No. Fleas | % Fleas | No. Fleas | % Fleas | No. Fleas | % Fleas | No. Fleas | % Fleas | No. Fleas | % Fleas | No. Fleas | % Fleas | No. Fleas | % Fleas | % |
|---|---|---|---|---|---|---|---|---|---|---|---|---|---|---|---|---|---|---|
| | | \multicolumn{18}{c}{Day Reinfested} |
| | | 0 | | 1 | | 2 | | 3 | | 4 | | 7 | | 8 | | 9 | | 10 |
| 915 | 0.0 | 6 | 12.0% | 2 | 4.0% | 6 | 12.0% | 23 | 46.0% | 33 | 66.0% | 28 | 56.0% | 14 | 28.0% | 18 | 36.0% | |
| 3162 | 0.0 | 5 | 10.0% | 6 | 12.0% | 8 | 16.0% | 10 | 20.0% | 33 | 66.0% | 34 | 68.0% | 24 | 48.0% | 17 | 34.0% | |
| 1203 | 2.0 | 1 | 2.0% | 0 | 0.0% | 0 | 0.0% | 0 | 0.0% | 9 | 18.0% | 0 | 0.0% | 28 | 56.0% | 13 | 26.0% | |
| 1267 | 2.1 | 0 | 0.0% | 0 | 0.0% | 0 | 0.0% | 0 | 0.0% | 24 | 45.0% | 1 | 2.0% | 8 | 16.0% | 6 | 12.0% | |
| 1218 | 21.2 | 0 | 0.0% | 0 | 0.0% | 0 | 0.0% | 0 | 0.0% | 0 | 0.0% | 0 | 0.0% | 0 | 0.0% | 0 | 0.0% | |
| 3325 | 22.1 | 1 | 2.0% | 0 | 0.0% | 0 | 0.0% | 0 | 0.0% | 0 | 0.0% | 0 | 0.0% | 0 | 0.0% | 0 | 0.0% | |
| 3164 | 54.3 | 1 | 2.0% | 0 | 0.0% | 0 | 0.0% | 0 | 0.0% | 0 | 0.0% | 0 | 0.0% | 0 | 0.0% | 0 | 0.0% | |
| 3404 | 53.1 | 0 | 0.0% | 0 | 0.0% | 0 | 0.0% | 0 | 0.0% | 0 | 0.0% | 0 | 0.0% | 0 | 0.0% | 0 | 0.0% | |
| Mean Controls | | 6 | 11.0% | 4 | 8.0% | 7 | 14.0% | 17 | 33.0% | 33 | 66.0% | 31 | 62.0% | 19 | 38.0% | 18 | 35.0% | |

TABLE 4-continued

Pyriproxifen Oral - Single Dose Residual Ovicidal Effect on Flea Eggs
Adult flea emergence from 50 flea eggs cultivated each test

| Cat No. | Dosage mg/kg | No. Fleas | % | No. Fleas | % | No. Fleas | % | No. Fleas | % | No. Fleas | % | No. Fleas | % | No. Fleas | % | No. Fleas | % |
|---|---|---|---|---|---|---|---|---|---|---|---|---|---|---|---|---|---|
| Mean Treated | | | | | | | | | | | | | | | | | |
| @ 2 mg/kg | | 1 | 1.0% | 0 | 0.0% | 0 | 0.0% | 0 | 0.0% | 17 | 33.0% | 1 | 1.0% | 18 | 36.0% | 10 | 19.0% |
| @ 21.5 mg/kg | | 1 | 1.0% | 0 | 0.0% | 0 | 0.0% | 0 | 0.0% | 0 | 0.0% | 0 | 0.0% | 0 | 0.0% | 0 | 0.0% |
| @ 53.7 mg/kg | | 1 | 1.0% | 0 | 0.0% | 0 | 0.0% | 0 | 0.0% | 0 | 0.0% | 0 | 0.0% | 0 | 0.0% | 0 | 0.0% |
| Efficacy | | | | | | | | | | | | | | | | | |
| @ 2 mg/kg | | | 91% | | 100% | | 100% | | 100% | | 50% | | 98% | | 5% | | 46% |
| @ 21.5 mg/kg | | | 91% | | 100% | | 100% | | 100% | | 100% | | 100% | | 100% | | 100% |
| @ 53.7 mg/kg | | | 91% | | 100% | | 100% | | 100% | | 100% | | 100% | | 100% | | 100% |

Day Reinfested

| Cat No. | Dosage | 11 | | 14 | | 15 | | 16 | | 17 | | 18 | | 21 | | 22 | |
|---|---|---|---|---|---|---|---|---|---|---|---|---|---|---|---|---|---|
| 915 | 0.0 | 14 | 28.0% | 24 | 48.0% | 19 | 38.0% | 23 | 0.0% | 23 | 46.0% | 15 | 30.0% | 21 | 42.0% | 16 | 32.0% |
| 3162 | 0.0 | 21 | 42.0% | 39 | 78.0% | 21 | 42.0% | 27 | 0.0% | 17 | 34.0% | 24 | 48.0% | 24 | 48.0% | 23 | 46.0% |
| 1203 | 2.0 | 22 | 44.0% | 30 | 60.0% | Terminated | | | | Terminated @ 15 days | | | | | | | |
| 1267 | 2.1 | 2 | 4.0% | 19 | 38.0% | Terminated | | | | Terminated @ 15 days | | | | | | | |
| 1218 | 21.2 | 0 | 0.0% | 0 | 0.0% | 0 | 0.0% | 0 | 0.0% | 2 | 4.0% | 1 | 2.0% | 23 | 46.0% | 16 | 32.0% |
| 3325 | 22.1 | 0 | 0.0% | 0 | 0.0% | 0 | 0.0% | 0 | 0.0% | 0 | 0.0% | 0 | 0.0% | 0 | 0.0% | 0 | 0.0% |
| 3164 | 54.3 | 0 | 0.0% | 0 | 0.0% | 0 | 0.0% | 0 | 0.0% | 0 | 0.0% | 0 | 0.0% | 0 | 0.0% | 0 | 0.0% |
| 3404 | 53.1 | 0 | 0.0% | 0 | 0.0% | 0 | 0.0% | 0 | 0.0% | 0 | 0.0% | 0 | 0.0% | 0 | 0.0% | 0 | 0.0% |
| Mean Controls | | 18 | 35.0% | 32 | 63.0% | 20 | 40.0% | 25 | 0.0% | 20 | 40.0% | 20 | 39.0% | 23 | 45.0% | 20 | 33.0% |
| Mean Treated | | | | | | | | | | | | | | | | | |
| @ 2 mg/kg | | 12 | 24.0% | 25 | 49.0% | 0 | 0.0% | 0 | 0.0% | Terminated @ 15 days | | | | | | | |
| @ 21.5 mg/kg | | 0 | 0.0% | 0 | 0.0% | 0 | 0.0% | 0 | 0.0% | 1 | 2.0% | 1 | 1.0% | 12 | 23.0% | 8 | 16.0% |
| @ 53.7 mg/kg | | 0 | 0.0% | 0 | 0.0% | 0 | 0.0% | 0 | 0.0% | 0 | 0.0% | 0 | 0.0% | 0 | 0.0% | 0 | 0.0% |
| Efficacy | | | | | | | | | | | | | | | | | |
| @ 2 mg/kg | | | 31% | | 22% | | 100% | | 100% | Terminated @ 15 days | | | | | | |
| @ 21.5 mg/kg | | | 100% | | 100% | | 100% | | 100% | | 95% | | 97% | | 49% | | 59% |
| @ 53.7 mg/kg | | | 100% | | 100% | | 100% | | 100% | | 100% | | 100% | | 100% | | 100% |

Day Reinfested

| Cat No. | Dosage | 23 | | 24 | | 25 | | 28 | | 29 | | 30 | | 31 | | 32 | |
|---|---|---|---|---|---|---|---|---|---|---|---|---|---|---|---|---|---|
| 915 | 0.0 | 36 | 72.0% | 41 | 82.0% | 33 | 66.0% | 23 | 46.0% | 20 | 40.0% | 41 | 82.0% | 42 | 84.0% | 43 | 86.0% |
| 3162 | 0.0 | 29 | 58.0% | 43 | 86.0% | 31 | 62.0% | 22 | 44.0% | 27 | 54.0% | 39 | 78.0% | 37 | 74.0% | 39 | 78.0% |
| 1203 | 2.0 | | | | | | | | | | | | | | | | |
| 1267 | 2.1 | | | | | | | | | | | | | | | | |
| 1218 | 21.2 | 11 | 22.0% | Terminated | | | | | | | | | | | | | |
| 3325 | 22.1 | 0 | 0.0% | 0 | 0.0% | 0 | 0.0% | 0 | 0.0% | 3 | 6.0% | 6 | 12.0% | 11 | 22.0% | 2 | 4.0% |
| 3164 | 54.3 | 0 | 0.0% | 0 | 0.0% | 1 | 2.0% | 2 | 4.0% | 3 | 6.0% | 5 | 10.0% | Terminated | | | |
| 3404 | 53.1 | 0 | 0.0% | 0 | 0.0% | 0 | 0.0% | 0 | 0.0% | 4 | 8.0% | Terminated | | | | | |
| Mean Control | | 33 | 65.0% | 42 | 84.0% | 32 | 64.0% | 23 | 45.0% | 24 | 47.0% | 40 | 80.0% | 40 | 79.0% | 41 | 82.0% |
| Mean Treated | | | | | | | | | | | | | | | | | |
| @ 2 mg/kg | | | | | | | | | | | | | | | | | |
| @ 21.5 mg/kg | | 6 | 11.0% | 0 | 0.0% | 0 | 0.0% | 0 | 0.0% | 3 | 6.0% | 6 | 12.0% | 11 | 22.0% | 2 | 4.0% |
| @ 53.7 mg/kg | | 0 | 0.0% | 0 | 0.0% | 1 | 1.0% | 1 | 2.0% | 4 | 7.0% | 5 | 10.0% | Terminated | | | |
| Efficacy | | | | | | | | | | | | | | | | | |
| @ 2 mg/kg | | | | | | | | | | | | | | | | | |
| @ 21.5 mg/kg | | | 83% | | 100% | | 100% | | 100% | | 87% | | 85% | | 72% | | 95% |
| @ 53.7 mg/kg | | | 100% | | 100% | | 98% | | 96% | | 85% | | 88% | Terminated | | | |

EXAMPLE 13

Tick control through the oral administration of an active ingredient

Technical grade pyriproxifen, 2-[1-methyl-2-(4-phenoxyphenoxy)ethoxyl pyridine, was diluted in corn oil and filled into gelatin capsules at two levels, 5% and 25%. The active ingredient loads were designed to provide nominal doses of about 30 and about 175 milligrams (mg) per kilogram (kg) body weight for each of four (4) rabbits, two in each group at each dose level. The test subjects were good tick hosts. Pyriproxifen solutions in corn oil were administered by gavage to four rabbits, two (2) in each group at each dose level (Table 5). Two additional rabbits were similarly administered corn oil as placebo control.

Ten (10) ticks (*Dermacentor variabilis*) were applied to each ear of each rabbit and enclosed in cotton ear bags to restrain the ticks and enable their recovery after engorgement. After application of the ticks, the ear bags were examined daily and the times at which male and female ticks became engorged and detached were recorded (Table 6).

Six (6) engorged female ticks, randomly collected from each group (A, B and C, total 18) were confined. After they laid their eggs, 100 eggs from each tick were observed every five days until ten days after the maximum larval hatch numbers had been obtained (Table 7).

TABLE 5

PYRIPROXIFEN INSECT GROWTH REGULATOR ORAL EFFECT ON FERTILITY OF TICK EGGS.

Rabbit treatments and dosages

| Rabbit No. | Rabbit Weight (kg) | Group/ Solution Code | Syringe Wt (gm) Before/After | Solution Dose gm | Solution Dose gm/kg | Pyriprox. Dose Total mg | Pyriprox. Dose Rate mg/kg |
|---|---|---|---|---|---|---|---|
| 1 | 2.75 | A/22.3s1 | 7.818 / 5.967 | 1.851 | 0.673 | 92.57 | 33.66 |
| 2 | 2.90 | A/22.3s1 | 7.816 / 5.949 | 1.867 | 0.644 | 93.37 | 32.20 |
| 3 | 2.75 | B/22.3s2 | 7.935 / 5.952 | 1.983 | 0.721 | 498.4 | 181.25 |
| 4 | 2.95 | B/22.3s2 | 7.887 / 5.884 | 2.003 | 0.679 | 503.5 | 170.66 |
| 5 | 2.55 | C/22.3s3 | 8.566 / 6.728 | 1.838 | 0.721 | 0 | 0.00 |
| 6 | 3.00 | C/22.3s3 | 7.764 / 5.898 | 1.866 | 0.622 | 0 | 0.00 |

TABLE 6

PYRIPROXIFEN INSECT GROWTH REGULATOR ORAL EFFECT ON FERTILITY OF TICK EGGS.

Tick attachment/Engorgement

| Rabbit No. | No. ticks attached Left Ear Male | No. ticks attached Left Ear Female | No. ticks attached Right Ear Male | No. ticks attached Right Ear Female | Cumulative engorged/detached Days after attachment 3 | 4 | 5 | 6 | 7 | 8 | 9 | 10 | 11 |
|---|---|---|---|---|---|---|---|---|---|---|---|---|---|
| 1 | 9 | 9 | 7 | 1 | 0 | 5 | 6 | 8 | 10 | 10 | 11 | 12 | 12 |
| 2 | 9 | 2 | 5 | 0 | 0 | 0 | 1 | 1 | 1 | 1 | 1 | 1 | 1 |
| 3 | 9 | 8 | 6 | 5 | 3 | 10 | 11 | 12 | 14 | 14 | 14 | 14 | 14 |
| 4 | 10 | 10 | 4 | 5 | 1 | 11 | 11 | 11 | 12 | 12 | 12 | 12 | 12 |
| 5 | 9 | 8 | 10 | 9 | 0 | 4 | 7 | 7 | 10 | 11 | 12 | 13 | 14 |
| 6 | 10 | 10 | 10 | 9 | 0 | 5 | 13 | 13 | 14 | 14 | 14 | 14 | 14 |

TABLE 7

PYRIPROXIFEN INSECT GROWTH REGULATOR ORAL EFFECT ON FERTILITY OF TICK EGGS.

Tick egg hatch, from 6 female ticks per rabbit group.

| Group | Tick No. | Cumulative tick egg hatch (%) on days after date of first tick engorgement 29 | 33 | 38 | 43 | 48 | 53 | 58 | 63 | Group Mean, ± Std Dev | Treatment Efficacy |
|---|---|---|---|---|---|---|---|---|---|---|---|
| A | 1 | 0 | 30 | 89 | 91 | 91 | 91 | 91 | 91 | 81.50 ± 11.70 | 17.8% |
|  | 2 | 0 | 1 | 63 | 71 | 71 | 71 | 71 | 71 |  |  |
|  | 3 | 0 | 48 | 67 | 67 | 67 | 67 | 67 | 67 |  |  |
|  | 4 | 0 | 1 | 91 | 92 | 92 | 92 | 92 | 92 |  |  |
|  | 5 | 0 | 0 | 72 | 72 | 72 | 72 | 72 | 72 |  |  |
|  | 6 | 0 | 5 | 96 | 96 | 96 | 96 | 96 | 96 |  |  |
| B | 1 | 0 | 3 | 85 | 86 | 86 | 86 | 86 | 86 | 47.17 ± 27.39 | 52.4% |
|  | 2 | 0 | 22 | 63 | 47 | 67 | 67 | 67 | 67 |  |  |
|  | 3 | 0 | 7 | 24 | 25 | 25 | 26 | 26 | 26 |  |  |
|  | 4 | 0 | 0 | 4 | 4 | 4 | 5 | 5 | 5 |  |  |
|  | 5 | 0 | 41 | 63 | 63 | 63 | 63 | 63 | 63 |  |  |

TABLE 7-continued

PYRIPROXIFEN INSECT GROWTH REGULATOR ORAL EFFECT
ON FERTILITY OF TICK EGGS.
Tick egg hatch, from 6 female ticks per rabbit group.

| Group | Tick No. | Cumulative tick egg hatch (%) on days after date of first tick engorgement | | | | | | | Group Mean, ± Std Dev | Treatment Efficacy |
|---|---|---|---|---|---|---|---|---|---|---|
| | | 29 | 33 | 38 | 43 | 48 | 53 | 58 | 63 | | |
| | 6 | 0 | 1 | 36 | 36 | 16 | 36 | 36 | 36 | | |
| C | 1 | 0 | 0 | 94 | 97 | 97 | 97 | 97 | 97 | 99.17 ± 1.07 | 0.0% |
| | 2 | 0 | 6 | 100 | 100 | 100 | 100 | 100 | 100 | | |
| | 3 | 0 | 0 | 100 | 100 | 100 | 100 | 100 | 100 | | |
| | 4 | 0 | 20 | 99 | 99 | 99 | 99 | 99 | 99 | | |
| | 5 | 0 | 0 | 94 | 99 | 99 | 99 | 99 | 99 | | |
| | 6 | 0 | 0 | 90 | 97 | 100 | 100 | 100 | 100 | | |

Ticks attached and engorged readily except on rabbit #2, from which only one (1) engorged tick was recovered. Egg hatch data (Table 7) showed that within 40 days after engorgement, most of the tick eggs had hatched. Efficacy was observed at the higher dose rate, since egg fertility was reduced to approximately half, compared with the fertility of eggs from ticks that had fed on the placebo-dosed control rabbits. Marginal reduction in egg fertility was also observed in eggs laid by ticks that had fed on rabbits treated at the lower dose rate. However, because of the wide variation in group egg fertility from almost complete sterility (5%) to marginal reduction (86%, compared with 100% control), differences between group egg fertilities were not statistically significant at the 95% probability level, at the doses tested. Nevertheless at the higher dose rate treatment 1 of 6 ticks was virtually sterilized (4–5% of eggs fertile), 2 more were partially sterilized (24–36% of eggs fertile) and the remaining 3 were partially sterilized (63–86% of eggs fertile) while control egg fertilities at the same times were more than 94%, and mostly 99–100%, for ticks feeding on control rabbits. The data suggest that complete tick sterilization would be expected at doses higher than those tested in this experiment.

EXAMPLE 14

Combination Gel

| COMPOSITION | AMOUNT (g) |
|---|---|
| Pyriproxifen | 50.0 |
| Milbemycin oxime | 1.3 |
| Cod Liver Oil | 12.5 |
| Corn Oil | 73.8 |
| Beef Peptone | 2.5 |
| Molasses | 5.0 |
| Glucose | 12.5 |
| Sodium Benzoate | 5.0 |
| Methyl Cellulose | 12.5 |
| Demineralized Water | 75.0 |

The pyriproxifen and milbemycin oxime are dissolved in the oil phase. The glucose, peptone, sodium benzoate and molasses are dissolved in the demineralized water heated to 60° C. into which the methyl cellulose is blended to form a gel, which is then blended with the oil phase. The gel is filled into flexible plastic squeeze tubes which are crimp sealed and capped. Alternatively, the gel may be filled into "dial-a-dose" syringes graduated to supply the desired daily dose rate/lb body weight.

This basic daily oral dose from gel may be improved by addition to vitamins (e.g., A, D, E and the B group), minerals, trace elements and essential fatty acids, to provide an easy-to-administer, complete nutritional supplement for pet animals that also provides effective heartworm and hookworm and ascarid prophylaxis and ectoparasite control by administering monthly one gram per 10 kg body weight.

EXAMPLE 15

Monolithic 300 mg implant

| COMPOSITION | AMOUNT (mg) |
|---|---|
| Pyriproxifen | 30.0 |
| Moxidectin | 1.0 |
| Methacrylate hydrophilic polymer | 60.0 |
| Elastomeric silicone composite | 240.0 |

The active ingredient is mixed with the prepared hydrophilic copolymer powder to which is added the silicone composite, for instance hydroxy-hydrogen-poly (dimethylsiloxane) and methyltriacetoxysiloxane cross linking agent in the proportions shown. The mixture is reacted at ambient temperature in a mold for 12 hours. Implants are sterilized by gamma radiation or by gassing with ethylene oxide after packaging. Implants are inserted subcutaneously either by trochar or by minor surgical procedure. Multiple implants may be inserted simultaneously depending on the animal's weight, on the known release rate of active ingredient, and on the desired frequency of reimplantation. The example single implant provides adequate blood levels for 90 days to sterilize all eggs laid by female fleas and preventing heartworm transmission by all mosquitoes feeding on an implanted dog weighing 6 kg. Multiple or larger implants may be administered to larger dogs, and implants may easily be removed after pay-out. By altering the physical characteristics of implants, longer pay-out and/or different release rates may be obtained.

Although the present invention and its advantages have been described in detail, it should be understood that various changes, substitutions and alterations can be made herein without departing from the spirit and scope of the invention as defined by the appended claims.

What is claimed is:

1. A composition comprising a pharmaceutically acceptable carrier for veterinary use, the composition being formulated to deliver an amount in the range of 0.001 mg to 1000 mg of compound per kilogram of animal body weight to produce when administered to a host animal an ovicidally effective amount of a compound having the formula:

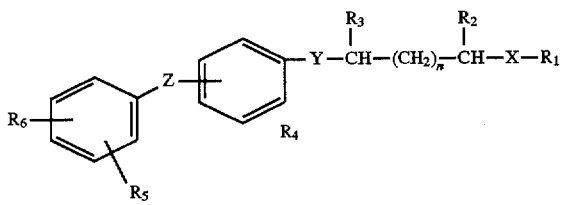

Wherein $R_1$ is selected from the group consisting of

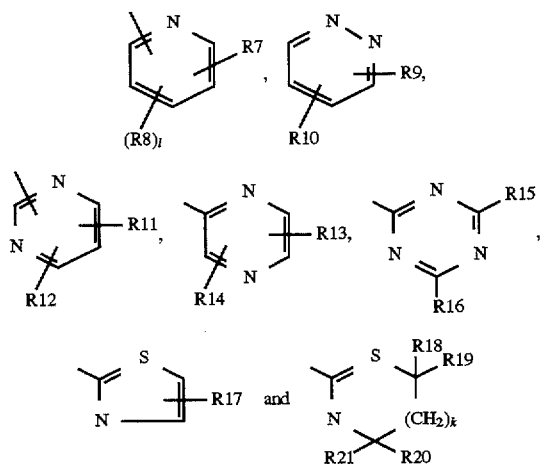

in which $R_7$, $R_8$, $R_9$, $R_{10}$, $R_{11}$, $R_{12}$, $R_{13}$, $R_{14}$, $R_{15}$, $R_{16}$, and $R_{17}$, are, the same or different, each a hydrogen atom, a halogen atom, a $C_1$–$C_4$ alkoxy group, a $C_1$–$C_4$ alkylthio group, trifluoro methyl group, or a nitro group; $R_{18}$, $R_{19}$, $R_{20}$ and $R_{21}$ are, the same or different, each a hydrogen atom, or a methyl group, k is an integer of 0 to 3; $R_2$ and $R_3$ are, the same or different, each a hydrogen atom, or a methyl group; $R_4$ is a halogen atom, or a methyl group, $R_5$ and $R_6$ are, the same or different, each a hydrogen atom, a halogen atom, a $C_1$–$C_4$ alkoxy group, or a $C_1$–$C_4$ haloalkyloxy group; X, Y and Z are, the same or different, each an oxygen atom, a sulfur atom or a methylene group, m is an integer of 0 to 4 and n is an integer of 0 to 2, in blood of the host animal.

2. A composition according to claim 1 and further comprising a pharmaceutically acceptable sustained delivery material.

3. A composition according to claim 2 wherein the sustained delivery material is 6 parts elastomeric silicone to 1 part hydrophilic methacrylate polymer.

4. A composition according to claim 2 wherein the compounds are pyriproxifen and moxidectin.

5. A composition according to claim 1 further comprising a preservative.

6. A composition according to claim 1 further comprising a flavoring.

7. A composition according to claim 1 further comprising a gel.

8. A composition according to claim 1 further comprising a vitamin.

9. A dietary supplement composition comprising a pharmaceutically acceptable carrier for veterinary use formulated to deliver an amount in the range of 0.001 mg to 1000 mg of compound per kilogram of animal body weight to produce when administered to a host animal in the host animal's blood an ovicidally effective amount of a compound having the formula:

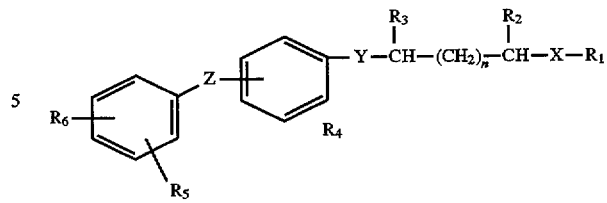

wherein $R_1$ is selected from the group consisting of

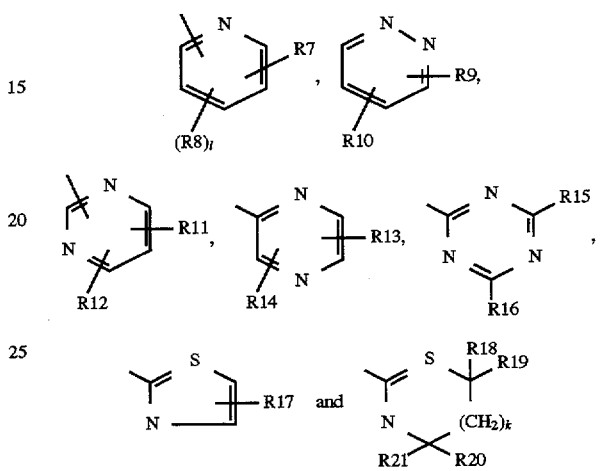

in which $R_7$, $R_8$, $R_9$, $R_{10}$, $R_{11}$, $R_{12}$, $R_{13}$, $R_{14}$, $R_{15}$, $R_{16}$, and $R_{17}$, are, the same or different, each a hydrogen atom, a halogen atom, a $C_1$–$C_4$ alkoxy group, a $C_1$–$C_4$ alkylthio group, trifluoro methyl group, or a nitro group; $R_{18}$, $R_{19}$, $R_{20}$ and $R_{21}$ are, the same or different, each a hydrogen atom, or a methyl group, k is an integer of 0 to 3; $R_2$ and $R_3$ are, the same or different, each a hydrogen atom, or a methyl group; $R_4$ is a halogen atom, or a methyl group, $R_5$ and $R_6$ are, the same or different, each a hydrogen atom, a halogen atom, a $C_1$–$C_4$ alkoxy group, or a $C_1$–$C_4$ haloalkyloxy group; X, Y and Z are, the same or different, each an oxygen atom, a sulfur atom or a methylene group, m is an integer of 0 to 4 and n is an integer of 0 to 2, which is transmitted to an ectoparasite feeding on the animal's blood.

10. A dietary supplement according to claim 9 wherein the compounds selected are pyriproxifen in the range of about 0.01 mg/kg to about 200 mg/kg and milbemycin in the range of about 0.5 mcg/kg to about 100 mg/kg.

11. A dietary supplement according to claim 9 wherein the compounds selected are pyriproxifen in the range of about 0.01 mg/kg to about 200 mg/kg and ivermectin in the range of about 0.5 mcg/kg to about 100 mg/kg.

12. A dietary supplement according to claim 9 wherein the compounds selected are pyriproxifen in the range of about 0.01 mg/kg to about 200 mg/kg and milbemycin oxime in the range of about 0.5 mcg/kg to about 100 mg/kg.

13. A dietary supplement according to claim 9 wherein the compounds selected are pyriproxifen and moxidectin in the range of about 0.5 mcg to about 100 mg/kg.

14. The composition of claim 1 wherein the composition is formulated to deliver a dosage of from 0.01 mg to 100 mg per kilogram of animal body weight to the animal.

15. The composition of claim 1 wherein the composition is formulated to deliver a dosage of from 0.01 mg to 70 mg per kilogram of animal body weight to the animal.

16. The composition of claim 1 wherein the composition is formulated to deliver a dosage of from 0.02 mg to 50 mg per kilogram of animal body weight to the animal.

17. The composition of claim 1 wherein the composition is formulated to deliver the dosage to the animal by a transdermal transmission.

18. The composition of claim 17 wherein the composition is formulated as a spoton or a pouron formulation.

19. The composition of claim 1 wherein the composition is formulated to deliver a sustained release dosage to the animal.

20. The dietary supplement composition of claim 9 wherein the composition is formulated to deliver a dosage of from 0.01 mg to 100 mg per kilogram of animal body weight to the animal.

21. The dietary supplement composition of claim 9 wherein the composition is formulated to deliver a dosage of from 0.01 mg to 70 mg per kilogram of animal body weight to the animal.

22. The dietary supplement composition of claim 9 wherein the composition is formulated to deliver a dosage of from 0.02 mg to 50 mg per kilogram of animal body weight to the animal.

23. The dietary supplement composition of claim 9 which further comprises one or more additives selected from the group consisting of a preservative, a vitamin, a mineral and an Omega 3 fish oil, each in a physiologically effective amount.

24. A composition comprising pyriproxifen formulated to deliver a sufficient amount of pyriproxifen to the blood of a host animal to provide an ovicidally effective concentration to an ectoparasite feeding on the blood of the animal.

25. A composition formulated as a single dose in the range of about 10 to 200 mg/kg of 2-[1-methyl-2-(4-phenoxyphenoxy)ethoxy]pyridine (pyriproxifen) with a pharmaceutically acceptable carrier chosen to deliver an ovicidally effective amount to the animal's blood stream for at least 25 days.

26. A composition according to claim 25 which further comprises 0.5 mcg/kg to 100 mg/kg of a parasite control compound selected from the group consisting of avermectin, avermectin derivatives, milbemycin, milbemycin derivatives, ivermectin, ivermectin derivatives, milbemycin oxime, milbemycin oxime derivatives, moxidectin, and moxidectin derivatives, or mixtures thereof.

27. A composition according to claim 25 formulated as an implant.

28. A composition according to claim 26 formulated as an implant.

29. A composition according to claim 24 which comprises a dose in the range of 0.001 to 1000 mg/kg of host animal body weight.

30. A composition according to claim 29 wherein the dose is in the range of 0.1 to 100 mg/kg.

31. A composition according to claim 29 wherein the dose is in the range of 0.1 to 50 mg/kg.

32. A composition according to claim 24 wherein the dose is formulated for oral administration.

33. A composition according to claim 29 wherein the dose is formulated for sustained release.

34. A composition according to claim 1 which comprises a parasiticidally effective amount of a compound selected from the group consisting of avermectin, avermectin derivatives, milbemycin, milbemycin derivatives, ivermectin, ivermectin derivatives, milbemycin oxime, milbemycin oxime derivatives, moxidectin, and moxidectin derivatives, or mixtures thereof.

35. A composition according to claim 9 which comprises a parasiticidally effective amount of a compound selected from the group consisting of avermectin, avermectin derivatives, milbemycin, milbemycin derivatives, ivermectin, ivermectin derivatives, milbemycin oxime, milbemycin oxime derivatives, moxidectin, and moxidectin derivatives, or mixtures thereof.

* * * * *